(12) United States Patent
Knight et al.

(10) Patent No.: US 6,589,166 B2
(45) Date of Patent: Jul. 8, 2003

(54) CARDIAC STABILIZER DEVICE HAVING MULTIPLEXED VACUUM PORTS AND METHOD OF STABILIZING A BEATING HEART

(75) Inventors: Gary Knight, West Chester, OH (US); William D. Fox, New Richmond, OH (US); Dale R. Schulze, Lebanon, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/785,590

(22) Filed: Feb. 16, 2001

(65) Prior Publication Data

US 2002/0115911 A1 Aug. 22, 2002

(51) Int. Cl.⁷ ................................................. A61B 1/32
(52) U.S. Cl. ..................... 600/205; 600/210; 600/229; 600/232; 600/231; 600/235
(58) Field of Search ................................. 600/201, 205, 600/210, 228, 229, 231, 232, 233, 235, 37

(56) References Cited

U.S. PATENT DOCUMENTS

| | | |
|---|---|---|
| 4,048,990 A | 9/1977 | Goetz |
| 4,350,160 A | 9/1982 | Kolesov et al. |
| 5,108,412 A | 4/1992 | Krumeich et al. |
| 5,119,804 A | 6/1992 | Anstadt |
| 5,131,905 A | 7/1992 | Grooters |
| 5,437,651 A | 8/1995 | Todd et al. |
| 5,484,391 A | 1/1996 | Buckman, Jr. et al. |
| 5,509,890 A | 4/1996 | Kazama |
| 5,571,074 A | 11/1996 | Buckman, Jr. et al. |
| 5,582,580 A | 12/1996 | Buckman, Jr. et al. |
| 5,727,569 A | 3/1998 | Benetti et al. |
| 5,749,892 A | 5/1998 | Vierra et al. |
| 5,807,243 A | 9/1998 | Vierra et al. |
| 5,836,311 A | 11/1998 | Borst et al. |
| 5,865,730 A | 2/1999 | Fox et al. |
| 5,885,271 A * | 3/1999 | Hamilton et al. ....... 600/201 X |
| 5,894,843 A | 4/1999 | Benetti et al. |
| 5,906,607 A | 5/1999 | Taylor et al. |
| 5,927,284 A | 7/1999 | Borst et al. |
| 6,015,378 A | 1/2000 | Borst et al. |
| 6,017,304 A | 1/2000 | Vierra et al. |
| 6,139,492 A | 10/2000 | Vierra et al. |
| 6,149,583 A | 11/2000 | Vierra et al. |
| 6,210,323 B1 | 4/2001 | Gilhuly et al. |
| 6,231,585 B1 | 5/2001 | Takahashi et al. |
| 6,251,065 B1 | 6/2001 | Kochamba et al. |
| 6,338,710 B1 | 1/2002 | Takahashi et al. |

FOREIGN PATENT DOCUMENTS

| | | |
|---|---|---|
| GB | 2 140 695 A | 12/1984 |
| WO | WO 94/0312 A1 | 2/1994 |
| WO | WO 00/15119 A2 | 3/2000 |

OTHER PUBLICATIONS

Kolessov V.I., The Surgery of Coronary Arteries of the Heart, Leningrad, Meditsina, 1977, pp 360 (Russian Article).

Kolessov V.I., The Surgery of Coronary Arteries of the Heart, Leningrad, Meditsina, 1977, pp 360 (English Translation).

Anstadt et al., "Direct Mechanical Ventricular Actuation for Cardiac Arrest in Humans, A Clinical Feasibility Trial", The Cardiopulmonary Journal, vol. 100, Jul.–Dec. 1991, pp.86–92.

(List continued on next page.)

*Primary Examiner*—Jeffrey A. Smith
(74) *Attorney, Agent, or Firm*—Brian S. Tonko

(57) ABSTRACT

A cardiac stabilizer for use during cardiac surgery. The stabilizer has a cardiac engagement member having at least two vacuum ports, wherein each vacuum port is connected to a separate pressure tube. The pressure in each vacuum port is individually controlled by a multiplexing unit.

22 Claims, 7 Drawing Sheets

OTHER PUBLICATIONS

DelRossi, A.J., et al., "A New Retractor to Aid in Coronary Artery Surgery", Annals of Thoracic Surgery, vol. 36, No. 1, Jul. 1983, pp101–102.

Conolly, John E., "Assisted Circulation" The Textbook of Surgery, the Biological Basis of Modern Surgical Practice, 10th edition, 1972, pp. 2114–2023.

* cited by examiner

CARDIAC STABILIZER DEVICE HAVING MULTIPLEXED VACUUM PORTS AND METHOD OF STABILIZING A BEATING HEART

TECHNICAL FIELD

The field of art to which this invention relates is instruments for cardiac surgery, in particular, cardiac stabilizer devices and methods of using such stabilizers in cardiac surgical procedures.

BACKGROUND OF THE INVENTION

Open chest cardiac surgical procedures have become common in the treatment of heart disease. These procedures include, for example, coronary artery bypass graft surgery, heart valve replacement, anastomosis procedures, aneurysm repairs, etc. Many of these procedures can now be performed as closed chest procedures using endoscopic surgical instruments and minimally invasive techniques, and additional procedures are continually being adapted as minimally invasive procedures.

Of particular interest are coronary artery bypass graft (CABG) procedures, since these are the most commonly performed cardiac surgical procedures. In conventional CABG procedures, a section of saphenous vein is typically harvested from the patient's leg. As an alternative to using a section of vein, a section of the radial artery may be harvested and used. The harvested section of blood vessel is then used to bypass blockages or lesions in various coronary arteries by performing anastomosis procedures to connect the aorta to the distal or downstream sides of the blocked vessels, thereby re-establishing oxygenated blood flow to the areas of the heart muscle which had been deprived because of the blockages. Another procedure that is commonly use in CABG procedures is the harvesting of an internal mammary artery (IMA) as a source of oxygenated blood for a bypass graft procedure. The harvested end of the IMA is attached via an anastomosis to a section of cardiac artery distal to the lesion or blockage site.

CABG procedures have conventionally been performed by stopping the patient's heart and utilizing a cardiopulmonary bypass procedure, wherein blood is shunted from the peripheral vascular system around the heart and the lungs to an external pump and blood oxygenator, and then back to the peripheral vascular system. It is known that there are many disadvantages and side effects associated with cardiopulmonary bypass, although the potential life-saving benefits of the procedure outweigh the risks for most patients. It is believed that the severity of the side effects tends to increase with the duration of the procedure.

Accordingly, cardiac surgical procedures that utilized cardiopulmonary bypass have been designed to be as time efficient as possible.

In order to attempt to improve surgical outcomes of CABG procedures, there has been a recent trend toward beating heart surgery. A major advantage of beating heart surgery is that it eliminates the need for cardiopulmonary bypass. However, beating heart surgery offers challenges to the surgeon in completing the CABG procedure. In particular, in order to perform an anastomosis, delicate vessel attachment procedures must be performed while the heart is moving as it beats. It can be appreciated by those skilled in the art that the surface of a beating heart is in a constant state of motion with relatively large cyclic movements or displacements. Therefore, in order to conduct a beating heart cardiac operation, it is necessary to stabilize at least a portion of the beating heart in the area of the vessel anastomoses.

Cardiac stabilizers have been developed and are known in the art to provide effective heart stabilization during a CABG procedure in both beating heart and stopped heart procedures. The stabilizers typically have an elongated tube or shaft with a pair of feet, or an arcuate member, mounted transversely to the distal end of the shaft. The feet are typically articulable with respect to the shaft in order to adjust to the contoured surfaces of the heart. In order to provide for improved cardiac stabilization, it is known to add vacuum ports to the feet, which are connected to a vacuum source in the tube. It is believed that the vacuum causes the surface of cardiac tissue adjacent to a vacuum port to be engaged by that port, thereby assisting in the stabilization of the beating heart. Another type of cardiac stabilizer is disclosed in U.S. Pat. No. 5,865,730, which is incorporated by reference. This stabilizer uses downward force to stabilize the heart while having a vacuum source connected to the tube to assist in stabilizing the heart, as well as providing a pathway to remove fluids and loose tissue in the vicinity of the anastomosis sites.

Although utilizing vacuum with a mechanical stabilizer has been shown to be advantageous, there may be side effects associated with the use of vacuum. For example, if the vacuum source is too intense or applied for an extended period of time, myocardial hematomas may be formed in the myocardial tissue in and about the vacuum port areas. The formation of myocardial hematomas is undesirable because they may be associated with myocardial cell damage and healing by fibrosis, resulting in reduced contractility at the site of application, and other known complications.

Accordingly, there is a need in this art for improved heart stabilizers that utilize vacuum to stabilize a heart and which minimize or eliminate the incidence of side effects such as the development of hematomas on the heart and damage to the subjacent myocardium during a stabilization procedure.

DISCLOSURE OF THE INVENTION

It is an object of the present invention to provide a cardiac stabilizer device that when used with a vacuum decreases the incidence of hematomas on and beneath the surface of the heart.

It is yet another object of the present invention to provide a method of stabilizing a heart with a cardiac stabilizer using a multiplexed vacuum source connected to the stabilizer.

Accordingly, a cardiac stabilizer device is disclosed. The cardiac stabilizer device has an elongated member having a proximal end and a distal end. At least one foot member is mounted to the distal end of the elongated member. The foot member has at least two tissue engagement vacuum port openings. At least two pressure tubes are mounted to the elongated member, the pressure tubes each have a proximal end, a distal and an inner lumen. Each vacuum port opening is in fluid communication with the lumen of one of pressure tubes so that the vacuum or pressure level in each port opening is individually controlled.

Another aspect of the present invention is a cardiac vacuum stabilizer having an articulable elongated member consisting of interlocking components or segments that are operable with each other. The articulable elongated member has a proximal end and a distal end. At least one foot member is mounted to the distal end of the elongated member. The foot member has at least two tissue engagement vacuum port openings. At least two pressure tubes are mounted to the elongated member, the pressure tubes each have a proximal end, a distal end, and an inner lumen. Each vacuum port opening is in fluid communication with the lumen of one of pressure tubes so that the vacuum or pressure level in each port opening is individually controlled. The elongated member may be locked into a fixed position by tensioning a flexible member associated with the elongated member.

Still yet another aspect of the present invention is a cardiac vacuum stabilizer. The cardiac stabilizer device has an elongated member having a proximal end and a distal end formed from at least two pressure tubes. At least one foot member is mounted to the distal end of the elongated member. The foot member has at least two tissue engagement vacuum port openings. The pressure tubes each have a proximal end, a distal end, and an inner lumen. Each vacuum port opening is in fluid communication with the lumen of one of pressure tubes so that the vacuum or pressure level in each port opening is individually controlled.

Yet another aspect of the present invention is the combination of the previously described cardiac stabilizers and a multiplexing vacuum source. The vacuum source cyclically varies or multiplexes the vacuum to each individual vacuum port from a high level effective for tissue engagement to a lower level effective to allow blood perfusion in the engaged cardiac tissue.

An additional aspect of the present invention is a method of stabilizing a beating heart during cardiac surgery. The method consists of initially providing a cardiac stabilizer device. The cardiac stabilizer device has an elongated member having a proximal end and a distal end. At least one foot member is mounted to the distal end of the elongated member. The foot member has at least two tissue engagement vacuum port openings. At least two pressure tubes are mounted to the elongated member. The pressure tubes each have a proximal end, a distal end, and an inner lumen. Each vacuum port opening of the foot member is in fluid communication with the lumen of one of the pressure tubes. The top of each pressure tube is connected to a source of vacuum. The foot member is rested upon the surface of a heart and engages and stabilizes the heart in the vicinity of the foot member. The vacuum in each tube is individually controlled so that cardiac tissue is engaged by each tissue engagement vacuum port and the pressure level varies cyclically in each vacuum port between a first negative pressure and a second higher pressure.

These and other aspects and advantages of the present invention will become more apparent from the accompanying drawings and following description.

DESCRIPTION OF THE PREFERRED EMBODIMENTS

Figure 1:
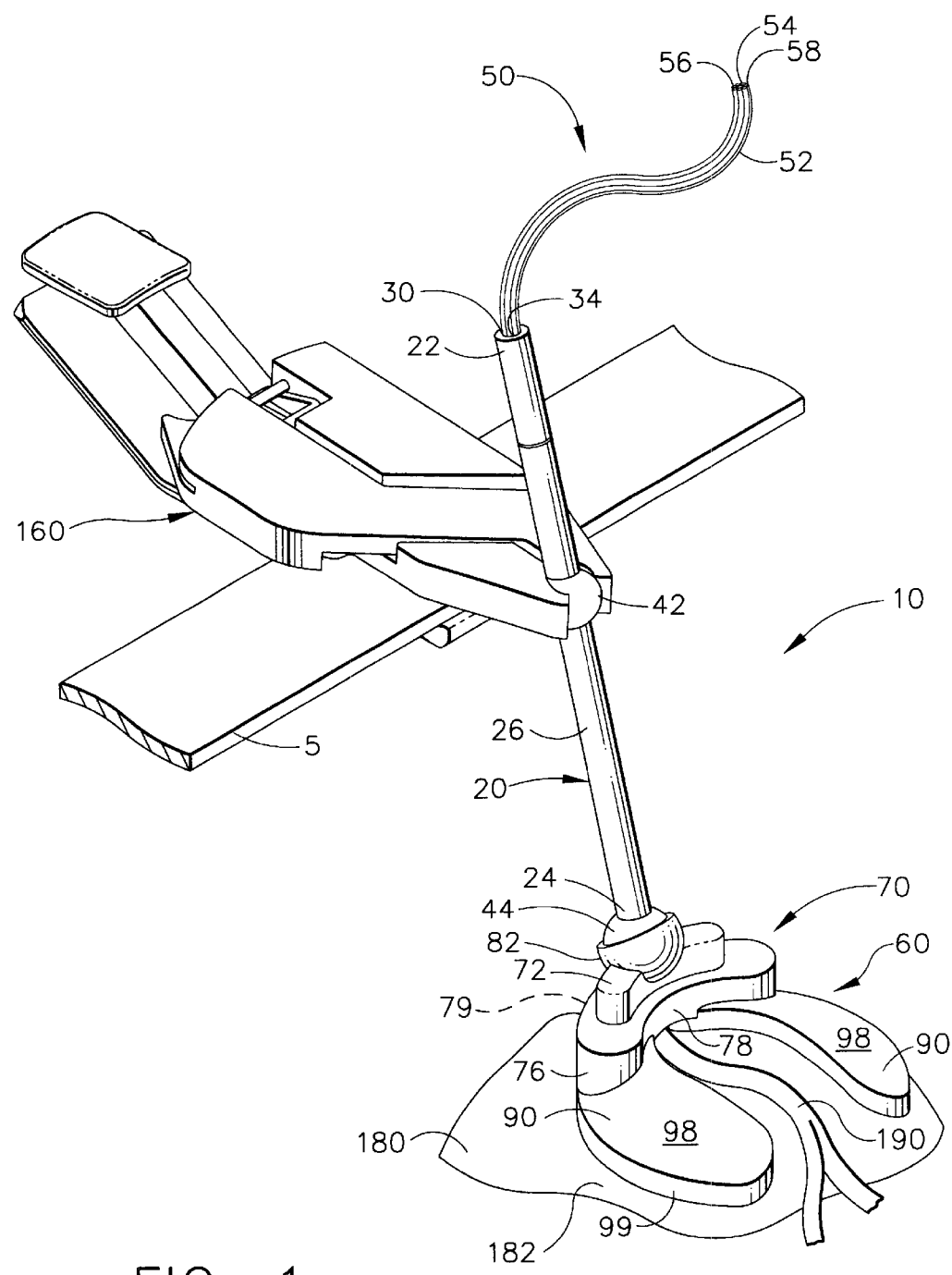
FIG. 1 is a perspective view of a cardiac stabilizer of the present invention engaging a section of cardiac muscle during an open chest cardiac surgical procedure; a coronary artery is seen between the feet of the device; pressure tubes are mounted in an interior lumen within the shaft.
Figures 2, 3:
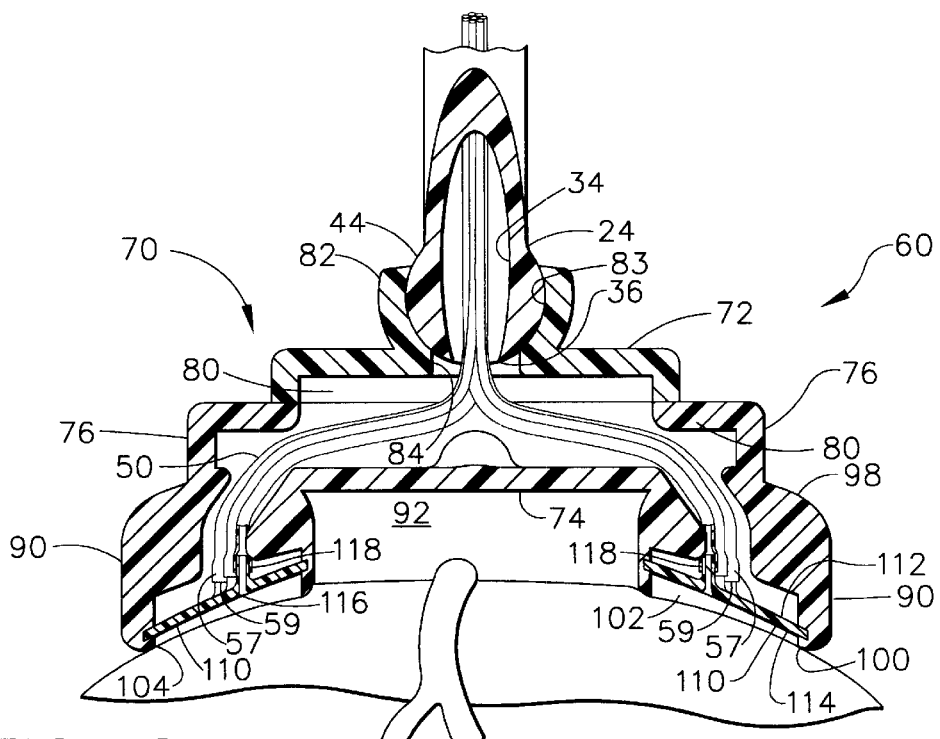
FIG. 2 is a partial cross-sectional view of the distal end of the stabilizer of FIG. 1, illustrating the pressure tubes and the vacuum ports, and also showing the feet of the stabilizer on the surface of the heart and the coronary artery located therebetween.
FIG. 3 is a partial bottom perspective view of the stabilizer of FIG. 1.

Referring now to FIGS. 1–3, a preferred embodiment of a cardiac stabilizer 10 of the present invention is illustrated. Cardiac stabilizer 10 is seen to have elongated shaft 20. Shaft 20 is seen to have proximal end 22 and distal end 24. The shaft 20 is seen to have an outer surface 26. Extending radially out from the surface 26 of the shaft 20 distal of proximal end 22 is a first ball member 42. Also extending radially out from the surface 26 of the shaft 20 at the distal end 24 is a second ball member 44. Ball members 42 and 44 are concentric with shaft 20. Shaft 20 is preferably made out of a substantially rigid material, but if desired may be made from a flexible material as well. Shaft 20 is further seen to have a proximal opening 30 in communication with a lumen 34. Shaft 20 is also seen to have a distal opening 36 in communication with lumen 34.

A plurality of pressure tubes 50 are seen to have exterior surfaces 52, interior passageways 54, proximal ends 56 and distal ends 57, and proximal openings 58 and distal openings 59. Pressure tubes 50 may be rigid or flexible, and may be made from conventional biocompatible materials known in this art including metals, metal alloys, elastomers, and polymers, or combinations thereof and the like.

Mounted to the distal end 24 of the shaft 20 is a heart engagement member 60, which is positioned on a heart surface 182 of a heart 180 of the surgical patient. Heart engagement member 60 is seen to have a frame member 70 having a top 72, a bottom 74, opposed ends 76 and front side 78 and rear side 79. Frame member 70 is further seen to be hollow and to have an interior vacuum plenum 80. Extending from the top 72 of frame member 70 is a hemispherically shaped cup member 82 having a cavity 83 for receiving second ball member 44, such that heart engaging member 60 is then articulably mounted to shaft 20. An opening 84 is seen to extend through top 72 into cavity 83 and to be in fluid communication with plenum 80 and cavity 83.

Extending down from the bottom 74 of frame member 70 are two vacuum foot members 90, although there may be one or more than two vacuum foot members 90. Each vacuum foot member 90 may be positioned near a coronary artery 190 as shown in FIG. 1, and is seen to be mounted to each end of the frame 70 and to be separated by a space 92. The foot members 90 are seen to be elongated members, preferably having a curved shape, although the members 90 may have other geometric shapes as well. Each foot member 90 is seen to have a distal end 94, a proximal end 96, a top surfaces 98, a bottom surface 100, and a side wall 99. Contained within the members 90 are a plurality of tissue engagement cavities 102 extending through to a like plurality of openings 104 that are in communication with cavities 102. Cavities 102 are separated by a plurality of rib members 106. Mounted in each cavity 102 is a plate member 110 having a top 112 and a bottom 114. Each plate member 110 is mounted in a cavity 102 in a conventional manner, for example, by having the periphery of plate member 110 contained in a groove in the interior surfaces of foot members 90, and the surfaces of rib members 106, or other conventional mounting methods can be used including welding, gluing, mechanical fastening, brazing and the like. Also, if desired, the plate members 110 may be formed as part of an integral casting with foot members 90. Contained in each plate member 110 is a passage 116 in fluid communication with the cavities 102 and plenum 80 and the openings 104. The section of the cavities 102 between the bottoms 114 of plate members 110 and openings 104 forms a vacuum engagement cell 120. The plates 110 are also seen to have proximal mounting tubes 118 having passages 119 for mounting the distal ends 57 of tubes 50. Each tissue engagement cavity 102 and cell 120 is in fluid communication with the lumen 58 of an individual tube 50, so that the pressure in each cavity 102 is controlled separately by a single pressure tube 50 in communication with that cavity. Articulation of heart engagement member 60 is provided by the second ball member 44 operably engaged in socket cup member 82, which together form a ball-type joint. Foot members 90 may have alternate configurations if desired, for example, circular or oval, rectangular, square or polygonal or combinations thereof. The foot members 90 may be flexible or semi-rigid thereby allowing them to be manually conformed to better fit the surface of the heart.

The stabilizer 10 is seen to be mounted to the retractor mount 160 which has a pair of arms 162 that engage first ball member 42 such that shaft 20 is articulable with respect to mount 160 and a retractor stabilizer bar 5. Mount 160 is mounted to the retractor stabilizer bar 5 which is part of a conventional sternal retraction device. A more detailed description of retractor mount 160 is contained in U.S. Pat. No. 5,865,730 which is incorporated by reference.

If desired, the pressure tubes of the stabilizer 10 may be mounted to the exterior surface 26 of the tube 20, for example, as a bundle, rather than running the tubes 50 through the lumen 34.

Figure 4:
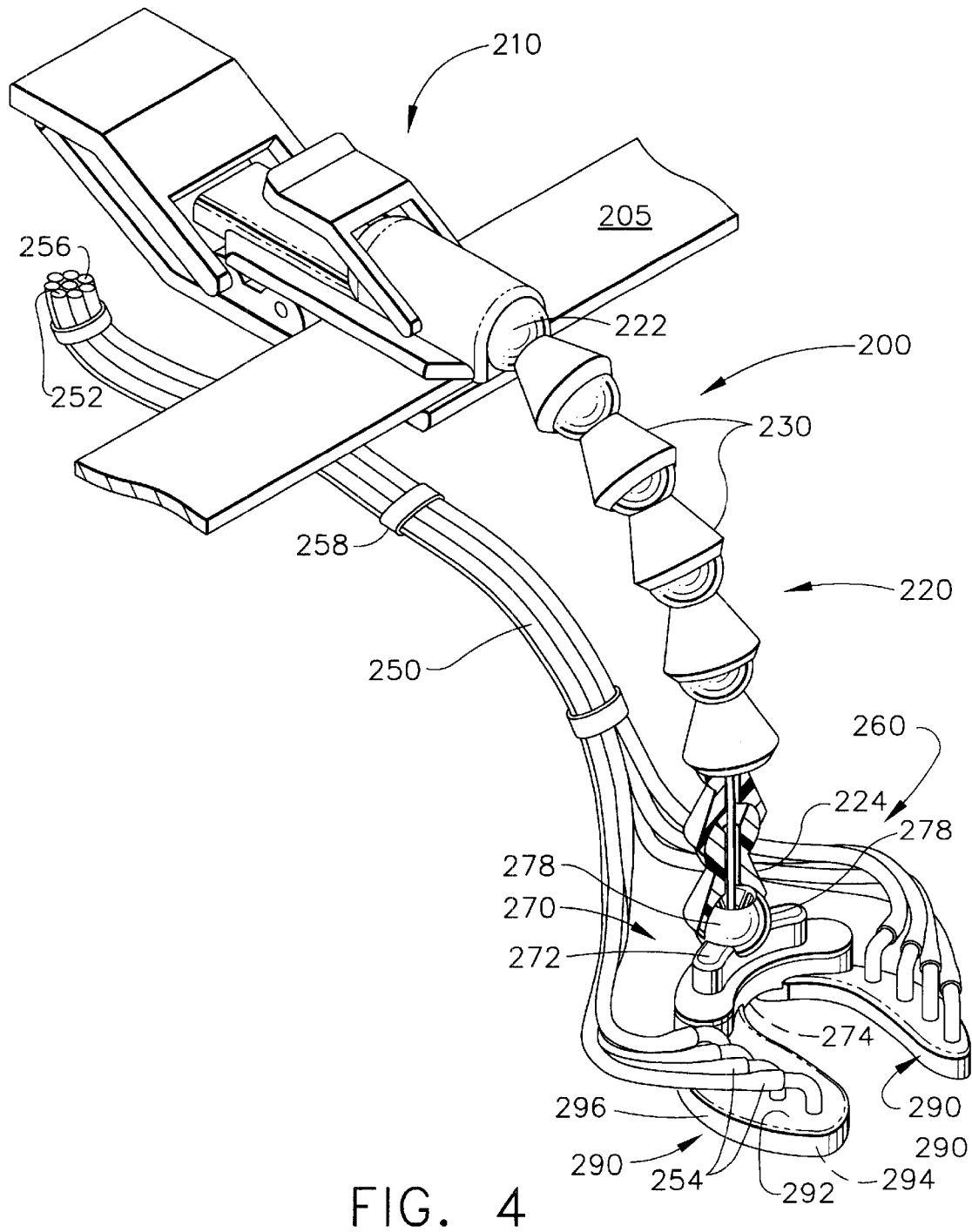
FIG. 4 is a perspective view of an alternate embodiment of a stabilizer of the present invention having a flexible, segmented shaft and pressure tubes mounted exterior to the shaft; the distal end of the shaft is illustrated in partial cross-section.
Figure 5:
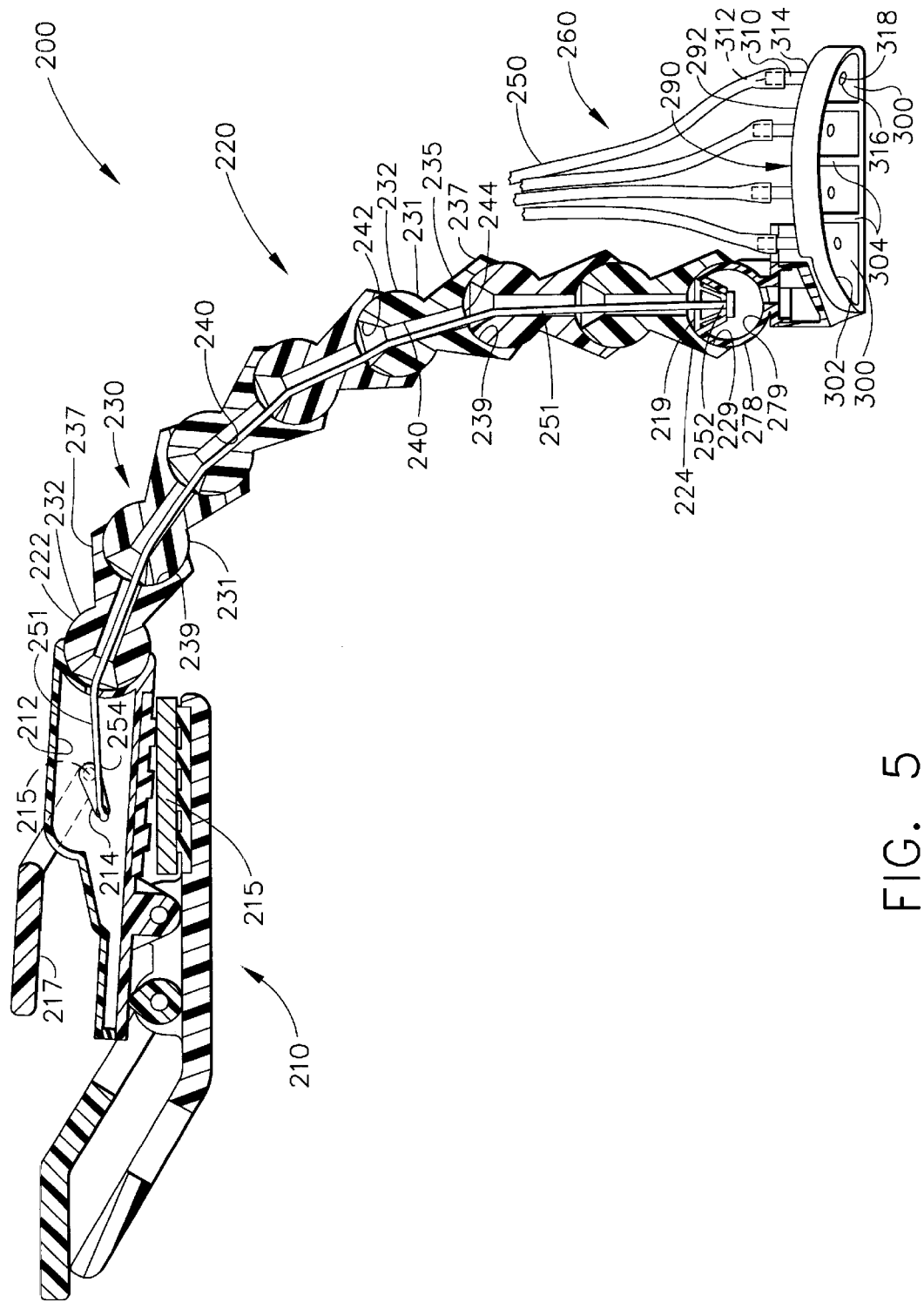
FIG. 5 is a cross-sectional view of the stabilizer of FIG. 4.

An alternate embodiment of a stabilizer 200 of the present invention is seen in FIGS. 4 and 5. The stabilizer 200 is seen to have an articulable arm 220 having proximal end 222 and distal end 224. The arm 220 is seen to be made up of a plurality of segments or link members 230. Each link member 230 is seen to have a frame 231 having a proximal spherical head section 232 and a distal socket cup section 237 having a hemispherical cavity 239. Each member 230 is seen to have a longitudinal passage 240 having a proximal opening 242 and a distal opening 244. The proximal spherical head 232 of each link member 230 is articulably or operably engaged in the cavity 239 of socket 237 of the distal flared end of each link 230 thereby forming the articulable arm 220. A control wire 250 having a distal end 252 and a proximal end 254 is seen to be threaded in and mounted through the passages 240 of the link members 230. A heart engagement member 260 is seen to be mounted to the distal end 224 of the arm 220. Heart engagement member 260 is seen to have a frame 270. Frame 270 has a top 272 and a bottom 274. Extending upward from the top 272 of the frame 270 is the spherical mounting member 278 for operably engaging the bottom 224 of the arm 220. Spherical member 278 is contained within the hemispherical cavity 239 of socket 237 of the distal most link member 230 of the arm 220. Extending from the bottom 274 of frame 270 are two foot members 290. There may one or more than two foot members 290 also. Each foot member 290 is seen to be elongated, partially curved members having a top surface 272, a bottom surfaces 294, and a side 296. Each member 290 is seen to have a cavity 300 in communication with an opening 302. The cavities 300 are separated by a plurality of rib members 304. Extending from the top surfaces 292 of the foot members 290 are seen to be a plurality of pressure tubes connecting members 310. Each connecting member 310 has a proximal end 312, a distal end 314, and a lumen 316 that is in fluid communication with an opening 318 that extends through member 290 into one of cavities 300, and is in fluid communication therewith.

Each of a plurality of pressure tubes 253 is seen to have a proximal end 252 and a distal end 254. Each of pressure tubes 253 has a lumens 256 and the distal end 274 is mounted to a proximal end 312 of one of the connecting members 310 such that the lumens 256 of the pressure tubes 250 are in fluid communication with the cavities 300 of foot members 90. Specifically, each pressure tube 250 is fluidly connected to a cavity 300.

The proximal end 222 of the arm 200 is seen to be articulably mounted to a retraction mounting member 210 which is mounted to a retractor stabilizer bar 205. The tubes 253 are optionally bundled together with at least one band member 258. The proximal end 254 of the wire 250 extends into cavity 212 of retractor mounting member 210 and is mounted to a pivot arm 214 which is connected by a pivot 215 to an exterior control arm 217. The distal end 252 of the control wire 250 is seen to be mounted in a cavity 279 of member 278 by fixing the end 252 to a basket retainer member 219. Control wire 50 may be replaced by any suitable flexible member or chain, and may be made from metals, polymers, combinations thereof and the like and may consist of one or more filaments, links and linkages and combinations thereof and the like.

When the control arm 217 is rotated upwardly, tension is released on the control wire 250 and the link members 230 are free to articulate and move. When the surgeon locates the foot member 290 on the surface of the heart, he rotates the lever arm 217 downwardly, thereby increasing tension on the control wire 250 and locking the link members 230 in a fixed configuration, and also locking the heart engagement member 260 in place. If desired, the pressure tubes 250 could be run through the passages 240 in the links 230.

Figure 6:
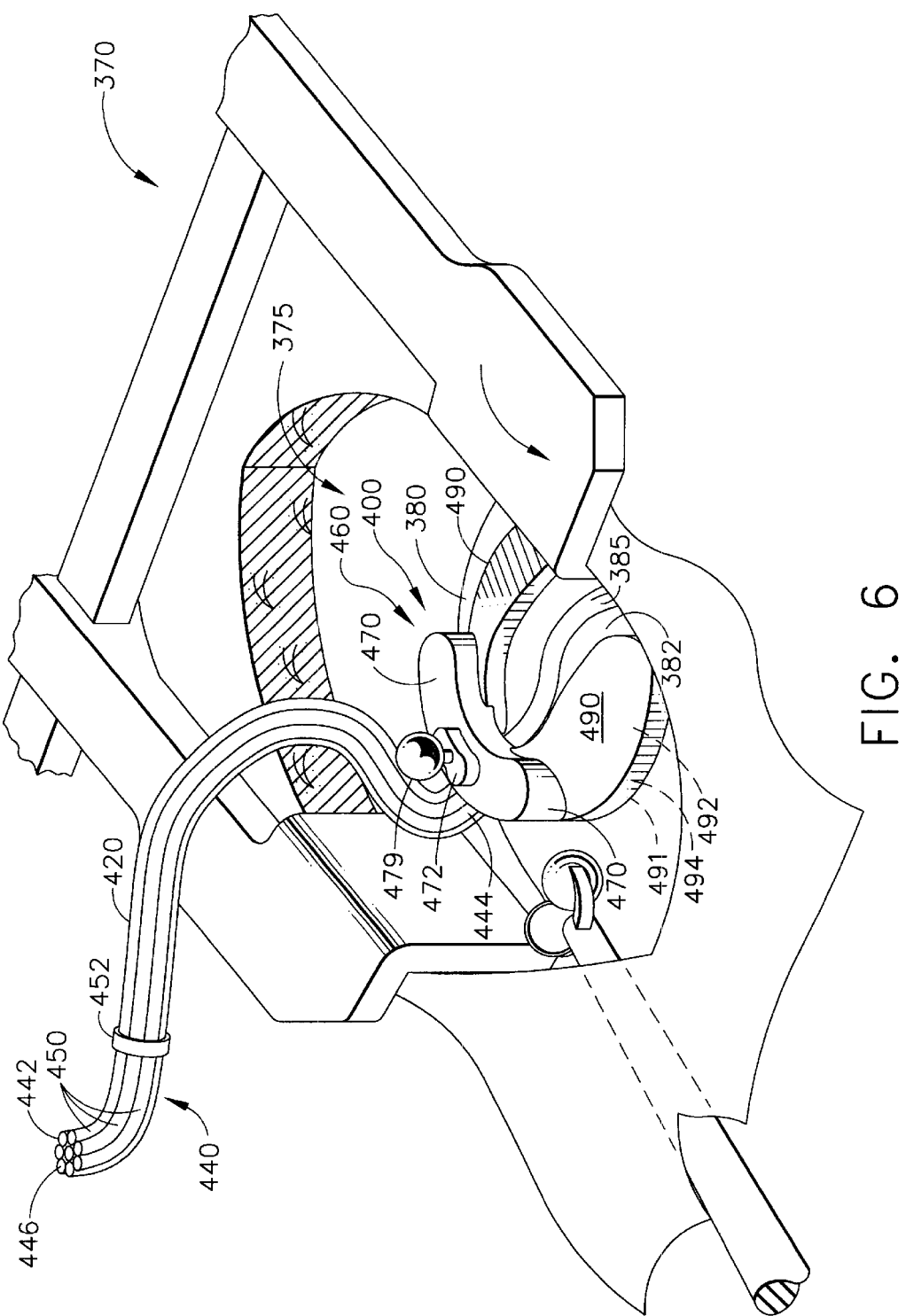
FIG. 6 is a perspective view of another alternate embodiment of a stabilizer of the present invention; the stabilizer shaft comprises a plurality of pressure tubes bundled together.

Referring now to FIG. 6, another alternate embodiment of the present invention, a vacuum stabilizer 400, is seen. A conventional retractor 370 is seen holding open a surgical incision 375 of a patient, exposing the patient's heart 380. The heart 380 is seen to have a surface 382 and a coronary artery 385. Stabilizer 400 is seen to have a plurality of pressure tubes 440 bundled together by band members 452 to form a shaft member 420. Each tube 440 is seen to have a proximal end 442, a distal ends 444, an internal passageway or lumen 446, and an outer surface 450. Mounted to the distal ends 444 of the shaft member 420, is an heart engagement member 460 having a frame 470 and two bottom foot members 490. There may be one or more than two bottom foot members 490. The heart engagement member 460 is articulable with respect to the shaft 420 by bending shaft 420. Shaft 420 is preferably constructed of biocompatible materials that take a set when bent. This enables shaft 420 to be used as a handle or to be attached to the surgical retractor in a similar manner as shown for the embodiment shown in FIG. 1. Shaft 420 may also be constructed of biocompatible materials that are flexible, such as polyurethane tubing. For such an embodiment, a stabilization grasper 480 with grasping cups 482 may be used with stabilizer 400. Grasping cups 482 are releasably clamped onto a positioning handle 479 extending upward from the top 472 of frame 470. Stabilizing grasper 480 may be inserted through a secondary incision 484 to optimize surgical access through incision 375. When constructing the shaft 420 from flexible tubes 440, an external bendable frame member (not shown) may be used to support the tubes 440.

Each distal end 444 of each pressure tubes 240 is mounted to the frame 470 of heart engagement member 460 so as to be in fluid contact with one of a plurality of tissue engagement cavities 492 and one of a plurality of bottom openings 494 contained in the bottom 491 of the foot members 490. The proximal ends 442 of tubes 440 are connected to a vacuum source.

Figure 7:
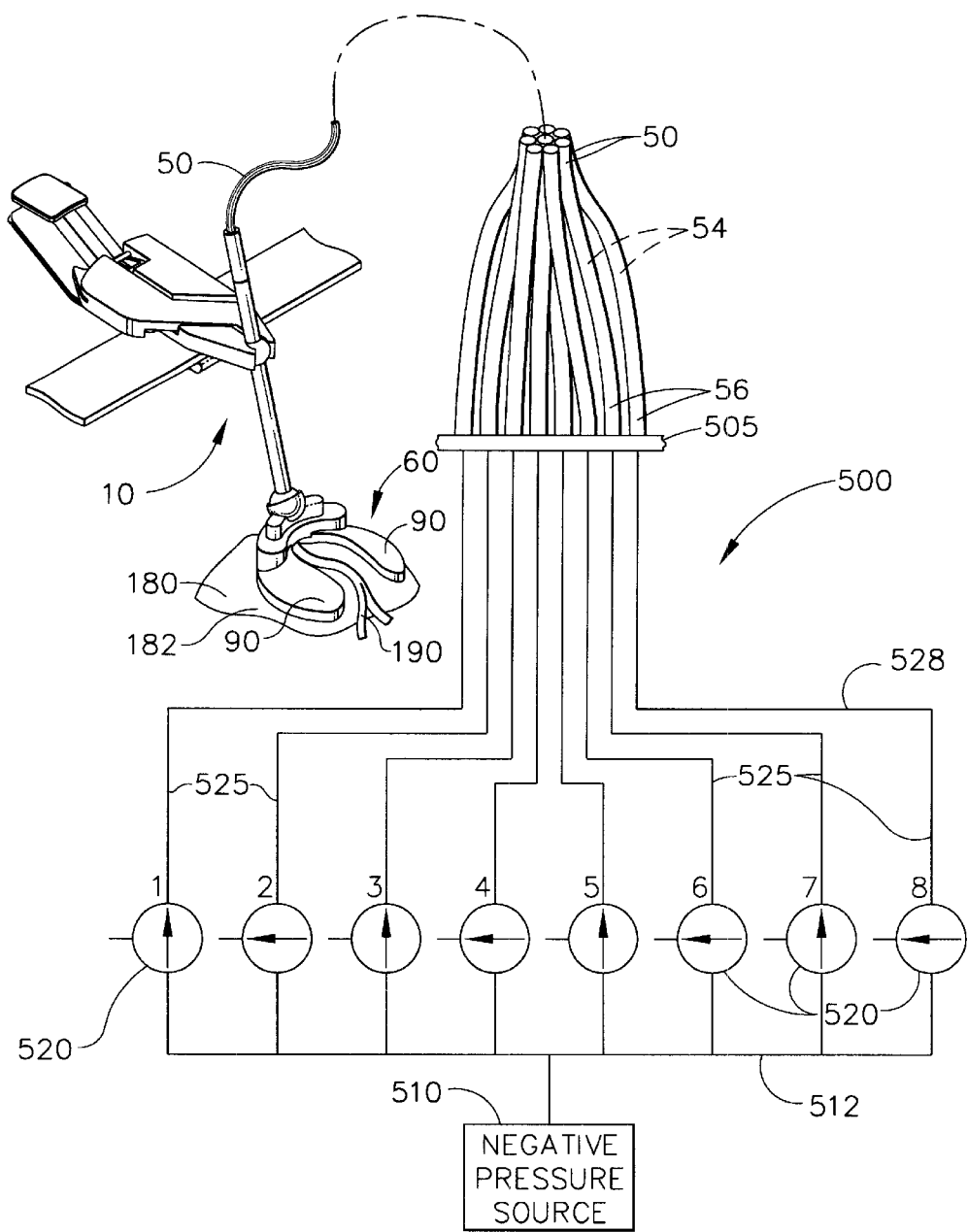
FIG. 7 is a flow diagram illustrating a multiplexing vacuum source and connection for use with the stabilizers of the present invention, wherein the pressure is alternated between negative and atmospheric.

The vacuum stabilizers of the present invention are used by connecting the pressure tubes of the stabilizer to a multiplexed vacuum source. Referring now to FIG. 7, stabilizer 10 (also shown in FIG. 1) of the present invention is illustrated mounted to a retractor stabilizer bar 5, wherein the heart engagement member 60 is engaging the surface 182 of a heart 180 with a coronary artery 190 positioned in space 92 between foot members 90. The proximal ends 56 of the pressure tubes 50 are mounted to a plurality of source mounting tubes 505 of a multiplex vacuum device 500, which is shown schematically. The vacuum or pressure level in the lumen 54 of each pressure tube 50 is pulsed on and off by the multiplex vacuum device 500, thereby pulsing the vacuum in each of the plurality of vacuum engagement cavities 102 of foot members 90. A flow diagram of a multiplexed vacuum device 500 connected to tubes 50 of stabilizer 10 of the present invention is illustrated in FIG. 7. As seen in FIG. 7, a vacuum source 510 (also referred to a negative pressure source 510) is connected to a manifold 512, which in turn is connected to a plurality of valves 520. Each of valves 520 may be an electrically actuated solenoid valve, or may be of various other types well known in the art such as, for example, electric motor actuated or pneumatically actuated drive valves, and the like. Each valve 520 is connected in turn to one of a plurality of pressure tube connectors 525, each of which connect to one of the vacuum source mounting tubes 505, to which one of tubes 50 is connected. The valves 520 are seen to be movable to a first position wherein the valve connects tube connector 525 to the vacuum source 510, and a closed position, wherein the vacuum source 500 is closed off and pressure tube connector 525 is in fluid communication with atmospheric pressure, and in turn, tube 50 and cavity 102 are fluidly connected to atmospheric pressure. The multiplexing of the vacuum source to each valve 520 is controlled by a conventional sequencing electronic controller which measures and controls the time that vacuum is supplied to each tube 50. Additional ways of providing a multiplexed vacuum source may be utilized as well. For example, pressure valves 520 may comprise a plurality of flexible tubes that are compressed to a closed position and released to an open position in a predetermined sequence by an electrically operated roller mechanism, thus fluidly connecting and disconnecting the vacuum source 510 to tubes 50.

Figure 8:
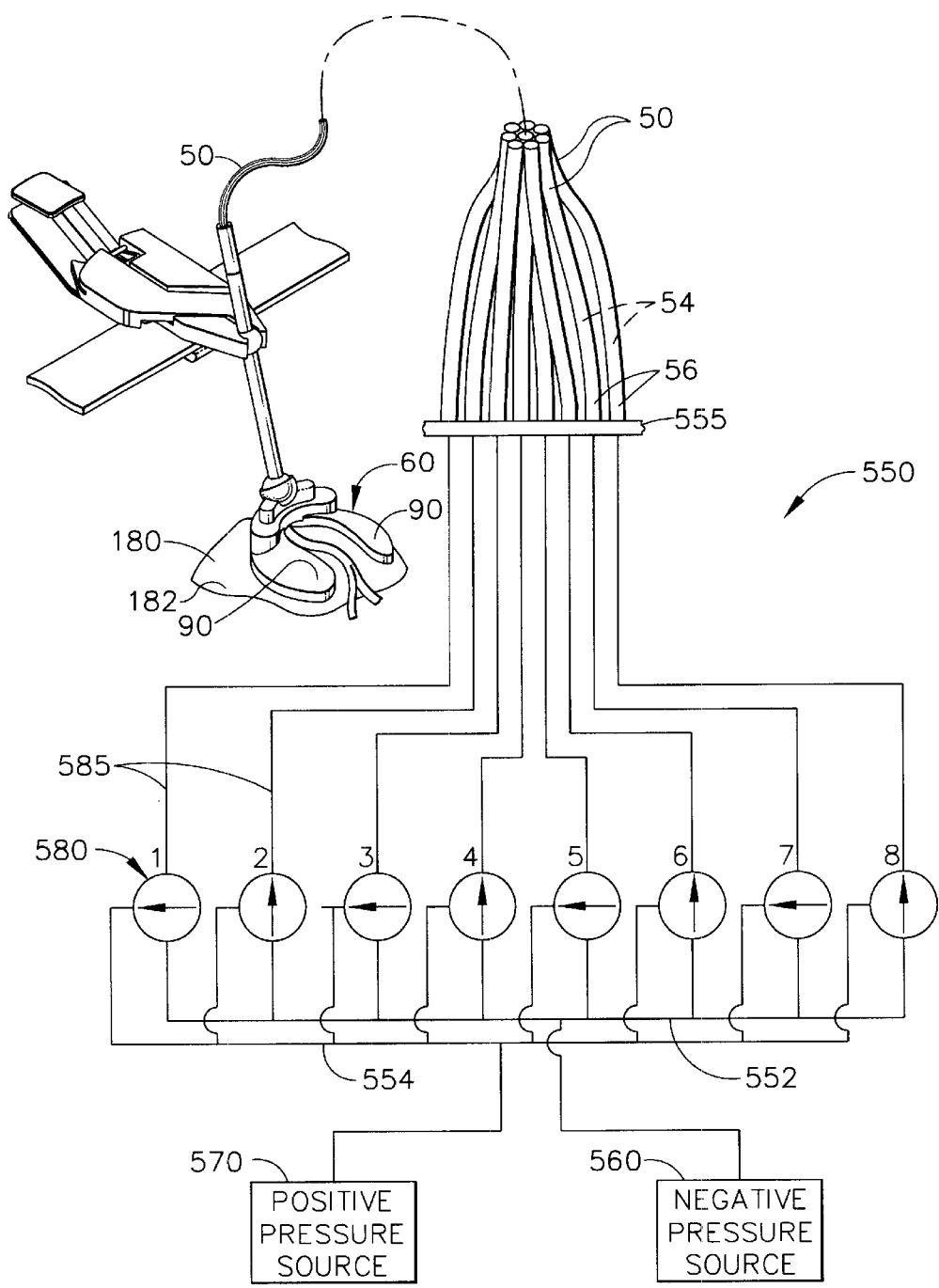
FIG. 8 is a flow diagram illustrating a multiplexing vacuum source and connection for use with stabilizers of the present invention, wherein the pressure is alternated between negative pressure and positive pressure.

In another alternative embodiment of the present invention, a multiplexed vacuum source 550 is used with stabilizer 10 as seen in FIG. 8. The heart engagement member 60 is engaging the surface 182 of a heart 180 with a coronary artery 190 positioned in space 92 between foot members 90. The proximal ends 56 of the pressure tubes 50 are mounted to a vacuum multiplexing device 550, which is shown schematically. The vacuum level in the lumen 54 of each pressure tube 50 is pulsed on and off by the multiplex vacuum device 550, thereby pulsing the vacuum in each of the plurality of cavities 102 of foot members 90. As seen in FIG. 8, a vacuum source 560 (also referred to as a negative pressure source 560) is connected to a manifold 552, which in turn is connected to a plurality of valves 580. As for the embodiment of the present invention described for FIG. 7, valves 580 may be solenoid valves or other types of electrically actuated valves, or pneumatically actuated valves, or one of other types of valves well known in the art. Each valve 580 is connected, in turn, to a one of a plurality of pressure tube connectors 585, which in turn is mounted to a one of a plurality of multiplex source connectors 555, to which one of plurality of pressure tubes 50 is connected. The multiplex vacuum device 550 is also seen to have a positive pressure source 570 connected to a manifold 554, which in turn is connected to each of plurality of valves 580. The valves 580 are seen to be movable to a first position wherein tube connectors 555 are fluidly connected to the vacuum source 560 so that pressure tubes 50 are fluidly connected to negative pressure, and to a second position, wherein the vacuum source 560 is closed off and pressure tube connector 555 is in fluid communication with positive pressure source 570, and in turn tube 50 and cavity 102 are fluidly connected to positive pressure. The multiplexing of the source 550 between vacuum source 560 and positive pressure source 570 to each valve 520 is controlled by a conventional sequencing electronic controller which measures and controls the time that vacuum and positive pressure are applied to each tube 50. The rate of pulsing and the duration of each pulse are determined to provide sufficient engagement of the cardiac tissue while providing for effective blood perfusion to prevent or substantially eliminate injury to the tissue of the heart.

The positive pressure source 570 may also be used in combination with a therapeutic agent mixed with the supply air or gas. For example, an anti-inflammatory agent may be vaporized and mixed with the air supply so that the heart surface engaged by the stabilizer may absorb small amounts of the mixture to help prevent inflammation of the tissue. Similarly, a topical anesthetic such as lidocaine may be vaporized and mixed with the air or gas supply to the positive pressure source 570, and thus supplied to the heart tissue to improve the recovery of the patient. Another therapeutic agent may be water or saline. Just by keeping the affected tissue moist is believed to be helpful in both maintaining a vacuum seal on the heart for stabilization, and for preventing injury to the tissue. Other therapeutic agents will become apparent to those skilled in the art. The amount of therapeutic agent absorbed by the heart tissue may be controlled not only by the rate the agent is supplied to the positive pressure source 570, but also by the frequency and duration of each negative-positive pressure cycle, which may be operator controlled.

Although not shown in a flow diagram, the multiplex source of the present invention can be constructed in a manner similar to that described above, however the source would switch between a first negative pressure source having a higher vacuum level and a second negative pressure source having a lower vacuum level.

The use of either of the multiplexed vacuum devices 500 and 550, in combination with the stabilizer devices of the present invention, is believed to prevent hematomas on the heart and other harmful side effects associated with vacuum stabilizers for the following reasons. First of all, the total time during the surgical procedure that the cardiac tissue engaged by the stabilizers is exposed to negative pressure is reduced. In addition, blood flow in the cardiac tissue within the vacuum ports or cavities of the stabilizers is improved when the vacuum is reduced or removed or positive pressure is engaged. And, tissue can re-perfuse during periods of decreased negative pressure or atmospheric or positive pressure. The addition of a therapeutic agent to the positive pressure source, such as water, saline, an anti-inflammatory drug, or a topical anesthetic such as lidocaine, is believe to contribute to preventing injury to the heart tissue and to improve recovery of the patient.

The vacuum which is used in the multiplex sources and methods of the present invention will be sufficient to provide effective tissue capture by the foot members of the stabilizers, while minimizing damage to the cardiac tissue. The vacuum levels will of course vary with the type and construction of the stabilizer (e.g., the number and size of the vacuum ports and tissue engagement cavities), and the individual characteristics of the patient's heart. For example, the vacuum may typically range from about 100 mmHg to about 400, more typically about 200 to about 350 and preferably about 250 to about 300, although once again these values are exemplary. Similarly, the pressure level supplied by the positive pressure source 570 may vary depending on the stabilizer, the patient, the type of surgical procedure, and the use of therapeutic agents, but is greater than ambient pressure and is approximately in the range, but not limited to, 50 to 200 mmHg. The cycling rate of the multiplex source will be sufficient to provide for effective tissue capture while effectively reducing or eliminating the incidence of hematomas. Once again, this will depend upon the particular stabilizer design, the vacuum levels, the use of positive or atmospheric pressure and the individual characteristics of the patient and the patient's heart. For example, typically, the cycle rate may be about 2 cycles/min to about 60 cycles/min, more typically about 4 cycles/min to about 30 cycles/min, and preferably about 6 cycles/min to about 15 cycles/min, although the cycle rate will vary depending upon circumstances.

If desired, the individual ports may have different levels of vacuum applied. In addition, the method of the present invention can be utilized with a cardiac stabilizer having a single pressure tube connected to a plurality of vacuum engagement ports such as that disclosed in U.S. Pat. No. 5,865,730. When used with such a stabilizer a single pressure tube would be connected to the multiplexing source, and the pressure in each vacuum port of the stabilizer would be simultaneously cycled between the same pressure levels.

Those skilled in the art will appreciate that although it is preferred to use the devices and methods of the present invention in conjunction with stabilizing and treating a heart during cardiac surgical procedures, the devices and methods are also suitable and useful for stabilizing and treating other body organs during a variety of surgical procedures.

The following example is representative of the principle and practice of the present invention although not limited thereto:

EXAMPLE

A patient is prepared for open beating-heart surgery in a conventional manner. The sternum is cut using a conventional bone saw in a conventional manner, and then a conventional rib retractor is mounted to the patient's sternum and actuated such that the ribs are spread apart and the patient's beating heart is exposed. After the surface of the heart is exposed using conventional surgical techniques, a vacuum cardiac stabilizer of the present invention having multiplexing vacuum ports is mounted to the chest expander using conventional mounting devices. Next, a multiplexed vacuum source is connected to the distal ends of the pressure tubes of the stabilizer. The vacuum source has a maximum vacuum of 500 mmHg. The vacuum source is turned on and the foot of the stabilizer is positioned to engage the heart surface. Cardiac tissue is engaged by the vacuum ports. The surgeon then proceeds to perform a conventional by-pass by performing an anastomosis about the cardiac arteries stabilized by the stabilization device using a graft blood vessel. The vacuum source to each vacuum port in the stabilizer foot is cycled by a control unit at a rate of about 6/min such that the vacuum varies between about 50 mmHg to about 250 mmHg. The anastomosis is completed and the stabilizer device is removed after the vacuum source is turned off. The heart surface in the area stabilized by the foot of the cardiac stabilizer exhibits no hematomas. The patient's chest is then approximated in accordance with standard surgical procedures.

The vacuum stabilizers of the present invention and the methods of stabilizing a beating heart using the multiplexed vacuum stabilizers of the present invention have many advantages. These advantages include the having a stabilizer engagement foot that maintains an effective grip on cardiac tissue thereby maintaining cardiac stabilization. In addition, the vacuum multiplexing provides for the restoration of blood flow to tissue within the vacuum. It can be appreciated that the length of a typical cardiac coronary artery bypass graft procedure can last for several hours, and will vary in duration depending upon the patient and the nature of the procedure. Deprivation of blood in cardiac tissue for extended periods of time caused by vacuum engagement can have adverse consequences. The use of the devices and methods of the present invention also is believed to provide reduced incidence of cardiac tissue hematomas.

Although this invention has been shown and described with respect to detailed embodiments thereof, it will be understood by those skilled in the art that various changes in form and detail thereof may be made without departing from the spirit and scope of the claimed invention.

We claim:

1. A cardiac stabilizer device comprising:
   at least one foot member having at least two engagement cells and at least two vacuum port openings, at least one vacuum port opening being in fluid communication with each of the at least two engagements cells, the at least two engagements cells being defined by a bottom wall, an outer wall and at least one rib;
   a suction source; and
   at least two pressure tubes having a proximal end, a distal end, and an inner lumen, wherein the suction source is in fluid communication with the proximal ends of the pressure tubes and each vacuum port opening is in fluid communication with a distal end of a separate pressure tube.

2. The stabilizer of claim 1 wherein the shaft comprises a lumen and the pressure tubes are mounted in the lumen.

3. The stabilizer of claim 1, comprising an elongated shaft member having a proximal end and a distal end; the at least one foot member being connected to the distal end of the shaft member.

4. The stabilizer of claim 3 wherein the at least one foot member is articulably mounted to the distal end of the shaft.

5. The stabilizer of claim 1, comprising an articulable elongated shaft member having a proximal end and a distal end, the articulable member comprising a plurality of segments.

6. The stabilizer of claim 1, wherein at least one of the two engagement cells defines a volume that is different than the volume defined by a second engagement cell.

7. The stabilizer of claim 1, wherein the inner surfaces of the rib are non-tapered.

8. The stabilizer of claim 1, wherein the bottom wall, the outer wall and the at least one rib are formed of an intergral casting.

9. The stabilizer of claim 1, wherein the volume of at least two engagement cells defines the majority of the volume defined by the outer wall and the bottom wall.

10. A cardiac stabilizer device comprising:

an articulate elongated shaft member having a proximal end and a distance end, the articulate member comprising a plurality of segments, each segment having a proximal end, a distal end, and a passage therethrough, wherein the proximal and distal ends of the segments are operably associated;

at least one foot member mounted to the distal end of the elongated member, said member having at least two engagement cells and at least two vacuum port openings, at least one vacuum port opening being in fluid communication with each separate engagement cell, the at least two engagement cells being defined by a bottom wall, an outer wall and at least one rib;

a flexible elongated member mounted in the passages of the segments for tensioning the elongated member;

at least two pressure tubes having a proximal end, a distal end, and an inner lumen, wherein the proximal ends of the pressure tubes are in fluid communication with a suction source and each vacuum port opening is in fluid communication with a distal end of a seperate pressure tube.

11. The stabilizer of claim 10 wherein the foot member is articulably mounted to the distal end of the shaft member.

12. The stabilizer of claim 10, wherein the pressure tubes are mounted exterior to the shaft member.

13. The stabilizer of claim 10, wherein the pressure tubes are mounted in the passages of the segments.

14. A cardiac stabilizer device comprising:

an elongated member having a proximal end and a distal end, the elongated member comprising at least two pressure tubes, each pressure tube having a distal end, a proximal end and an inner lumen;

at least one foot member mounted to the distal end of the elongated member, said member having at least two vacuum port openings, the at least two engagement cells being defined by a bottom wall, an outer wall and at least one rib, at least one vacuum port opening being in fluid communication with each separate engagement cell; wherein each vacuum port opening is in fluid communication with a distal end of a separate pressure tube.

15. The stabilizer of claim 14 wherein the tubes are bendable.

16. The stabilizer of claim 14 wherein the tubes are flexible.

17. The stabilizer of claim 14 further comprising a support member associated with the pressure tubes.

18. A method of stabilizing a beating heart during beating heart cardiac surgery, comprising:

providing a cardiac stabilizer device, the device comprising;

an elongated member having a proximal end and a distal end;

at least one foot member mounted to the distal end of the elongated member, said member having at least two vacuum port openings; and at least two pressure tubes mounted to the elongated member, the pressure tubes having a proximal end, a distal end, and an inner lumen, wherein the distal end of each pressure tube is mounted to the foot member such that each port opening is in fluid communication with the inner lumen of a separate pressure tube;

connecting a pressure source directly to the proximal end of each pressure tube; and, cyclically varying the pressure in each tube from a first negative pressure level to a second higher non-atmospheric pressure level.

19. The method of claim 18 wherein the second pressure level is greater than atmospheric pressure.

20. The method of claim 18 wherein the second pressure level is negative.

21. A method of stabilizing a beating heart during beating heart cardiac surgery, comprising:

providing a cardiac stabilizer device, comprising at least one foot member having at least two engagement cells and at least two vacuum port openings, at least one vacuum port opening being in fluid communication with each separate engagement cell; and at least two pressure tubes having a proximal end, a distal end, and an inner lumen, wherein each vacuum port opening is in fluid communication with a distal end of a separate pressure tube;

connecting a pressure source directly to the proximal end of each pressure tube; and cyclically varying the pressure in each tube from a first negative pressure level to a second higher, non-atmospheric pressure level.

22. A method of stabilizing a beating heart during beating heart cardiac surgery, comprising:

providing a cardiac stabilizer device, comprising a foot member having at least one vacuum port opening, and a pressure tube being in fluid communication with the at least one vacuum port opening;

providing a valve connected at one outlet to a first negative pressure source and at a second outlet to a second, non-atmospheric pressure source;

placing the foot member on the surface of beating heart;

actuating the valve to vary the pressure supplied by the valve to the pressure tube from the pressure of the first pressure source to the pressure of the second pressure source.

* * * * *

UNITED STATES PATENT AND TRADEMARK OFFICE
CERTIFICATE OF CORRECTION

PATENT NO.     : 6,589,166 B2                                                          Page 1 of 1
DATED          : July 8, 2003
INVENTOR(S)    : Knight et al.

It is certified that error appears in the above-identified patent and that said Letters Patent is hereby corrected as shown below:

Column 11,
Line 14, please delete "distance" and insert -- distal --.
Line 48, please delete "vacuum port openings" and insert -- two engagement cells --.

Signed and Sealed this

Twenty-first Day of October, 2003

JAMES E. ROGAN
*Director of the United States Patent and Trademark Office*